United States Patent [19]

Mahooti

[11] Patent Number: 4,652,126
[45] Date of Patent: Mar. 24, 1987

[54] APPARATUS, METHOD AND SYSTEM FOR COLOR MEASUREMENT

[75] Inventor: M. Ted Mahooti, Woodbury, Conn.
[73] Assignee: Waterbury Cos., Inc., Waterbury, Conn.
[21] Appl. No.: 721,531
[22] Filed: Apr. 10, 1985
[51] Int. Cl.[4] ............................................. G01N 21/01
[52] U.S. Cl. .................................. 356/244; 73/864.91
[58] Field of Search ............. 356/244; 73/863, 864.91
[56] References Cited

U.S. PATENT DOCUMENTS 4,496,242  1/1985  Clough et al. ...................... 356/244

Primary Examiner—Eugene P. LaRoche
Assistant Examiner—Robert J. Pascal
Attorney, Agent, or Firm—Pennie & Edmonds

[57] ABSTRACT

An apparatus for reproducibly positioning an object within a color measurement instrument comprising a bracket for attachment to the instrument, a support to orient the object in a predetermined, fixed position and a method for varying the position of the object by moving the support in horizontal and/or vertical directions in order that the optimum color properties of the object may be determined. A quality control system which comprises a comparison of the optimal color values as measured for a first sample to the color values measured for a representative sample of a production run.

25 Claims, 3 Drawing Figures

APPARATUS, METHOD AND SYSTEM FOR COLOR MEASUREMENT

FIELD OF THE INVENTION

The invention relates to a method and apparatus for fixably positioning ornamental or decorative metal objects, such as metal plated buttons, in a manner such that reproducible quantitative color determinations may be performed by a color measuring instrument.

BACKGROUND OF THE INVENTION

The ability to measure factors relating to the appearance of metal plated objects is important and necessary to those engaged in appearance science, because the unaided human eye, although sensitive and discriminating, cannot make the qualitative and quantitative judgments which are necessary and suitable for reproducible records.

With respect to the prior art, gold and silver plated buttons have been standardized and specified according to their size, quantity of metal plated, and their color. All of the above standards have quantitative values according to their specifications, except for the color. This parameter is compared and interpreted visually against samples kept for reference purposes by the manufacturer and the customer. This procedure results in inconsistent color matching and has often resulted in disputes among manufacturers and their customers, rejections and costly and time-consuming reworking of these articles.

One reason for inconsistent color determinations is a phenomenon known as metamerism which occurs when two colors which match under the illuminant do *not* match under another illuminant. Also, the high intensity of the specular reflection from metal plated objects prevents the eye from discriminating between small differences in surface texture, especially when such an object is embossed and/or ornamented.

Due to the above mentioned considerations, the objective of those in the art has been to perfect a means by which one may quantitatively measure the color of a manufactured metal plated object. The Hunter Lab Scales, devised in 1958, have been found to be the most suitable color meter, based upon Ewald Hering's opponent colors theory of vision. This theory holds that the sensations of red and green, yellow and blue, and white and black are paired on specified retinal cone structures in the eye. Each cone substance evokes one sensation when it is changed (decomposed) by light and the paired color is sensed when the cone reforms or is re-synthesized to its original state.

Difficulties arise because instruments capable of quantitative measurements of brightness, geometric or chromatic attributes of appearance, such as color, gloss, opacity, haze, and whiteness or yellowness of articles, only work well with flat surfaces. Embossed or ornamented buttons are seldom fabricated flat, and are usually convex. Quantitative measurements by existing color instruments such as colorimeters cannot generate precise and reproducible results unless the buttons can be positioned in the instrument in a standardized, reproducible manner.

The applicant has discovered an apparatus and method which will enhance the measuring capabilities of color measuring devices. The invention is capable of positioning non-standard, embossed, or ornamented objects such as buttons or the like in order that quantitative and qualitative color comparisons may be reproducibly made. This positioning feature of the invention not only presents the specimen or object to the color measuring instrument in a standard and repeatable manner, but also allows for quantitative and qualitative recording of the position of the specimen or object in the color measuring instrument as well as the color properties of the specimen or object.

SUMMARY OF THE INVENTION

The invention relates to an apparatus for reproducibly positioning an object within a color measurement system which comprises means for attaching the apparatus to the color measurement system, means for orienting an object in a predetermined fixed position on support means, and means for determining the horizontal and vertical positions of the object. The horizontal and vertical positions of the object are variable by moving the support means in horizontal and/or vertical directions so that the optimum color properties of the object can be measured.

In one embodiment of the invention, the means for determining the horizontal and vertical positions of the object are micrometers. The object to be fixably positioned within the color measuring instrument is advantageously a button. The apparatus may be attached by means of a bracket to a color measuring device such as a colorimeter.

An alternative embodiment of the invention is an apparatus for supporting an object for reproducible color measurement comprising a bracket attached to the color measuring device, a platform, object orientation means fixably secured to the platform means, means for synchronizing the rotation of the platform with the rotation of the object horizontal position determination means, means to determine the horizontal position of the object, and means for determining the vertical position of the object. The means for determining the vertical position of the object is operable independent of the means for determining the horizontal position of the object and is also operable without changing the horizontal position of the object. The horizontal and vertical position determination means are variable by moving the platform means in horizontal and/or vertical directions so that the optimum color properties of the object can be determined.

A further aspect of the invention relates to the apparatus as described above wherein the means for synchronizing the rotation of the platform with the rotation of the horizontal position determination means comprises at least two guide pins. Again, micrometers may be used to determine the horizontal and vertical positions of the object in the apparatus as described above.

A further embodiment of the invention concerns a method for measuring the color properties of an object which comprises placing and orienting an object in a predetermined fixed position on the support means of an apparatus as previously described, attaching the apparatus to a color measurement system, varying the horizontal and vertical positions of the object by moving the support means in horizontal and/or vertical directions to obtain the optimum color properties of the object, and recording the horizontal and vertical positions of the object at the optimum color properties.

Advantageously, the object to be measured for color properties is a button and the apparatus is attached to the color measuring instrument by bracket means. Micrometers may be used to vary the vertical and horizontal positions of the object. The support means for the object may be a die which is configured for reception of the object. A preferred color measurement system is a colorimeter.

Another embodiment of the invention is a method for measuring the color of an object which comprises placing the object on orientation means of an apparatus as described above, synchronizing the rotation of the platform with the rotation of the horizontal position determination means, determining the horizontal position of the object, determining the vertical position of the object by means operable independent of the means for determining the horizontal position of the object and further being operable without changing the horizontal position of the object, varying the horizontal and vertical position of the orientation means by moving the platform means in horizontal and/or vertical directions so that optimum color properties are obtained.

Another embodiment of the present invention concerns an improvement in a method for measuring the color properties of an object which comprises reproducibly determining the optimum color properties of the object by providing an apparatus as described above wherein an object can be mounted on the mounting means in only one configuration and the horizontal and vertical position determination means can be preset to the predetermined position to display the optimum color properties of the object.

An alternate embodiment of the present invention is a quality control system which comprises predetermining the optimum color properties of a first object according to the method described above, selecting a representative sample of objects from a production run, measuring the color properties of each member of the representative sample at the orientations previously recorded for the first object and comparing the properties of the sample with those of the first object. The color properties of the sample objects may first be statistically averaged before comparison with the properties of the first object. Advantageously, the object whose color properties are to be determined may be a button.

BRIEF DESCRIPTION OF THE DRAWINGS

Further benefits and advantages of the invention will become apparent from a consideration of the following description given with reference to the accompanying drawing figures which specify and show preferred embodiments of the present invention, and wherein.

DETAILED DESCRIPTION OF THE PREFERRED EMBODIMENTS

Figure 1:
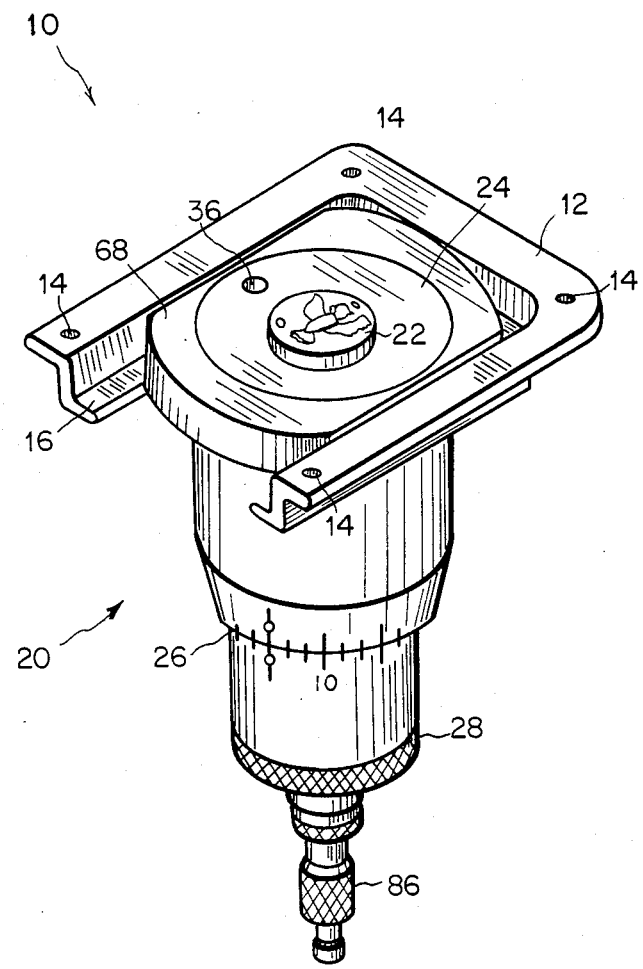
FIG. 1 is a perspective view of the apparatus of the invention.

Referring initially to FIG. 1, there is illustrated a specimen fixture assembly 10 constructed according to the present invention. This specimen fixture assembly 10 is designed for use with any standard color measuring instrument such as a Hunter Lab D-25 Colorimeter.

FIG. 1 provides a perspective view of the specimen fixture assembly, 10. This assembly 10 includes a bracket 12 for attachment to a color measuring instrument (not shown). The bracket, shown in a generally square configuration having one open end, is provided with a number of holes 14 to enable screw or bolt attachment to the instrument. The bracket also screw or bolt attachment to the instrument. The bracket also has a channel member or shelf 16 which supports the object fixture 20 in secured relation with respect to the instrument. The open end of the bracket 12 allows for insertion and removal of the fixture 20 by sliding it upon the shelf 16. This enables an operator to change objects on the fixture without removing the bracket 12 from the instrument.

The button or other object (not shown but see FIG. 2.) to be tested and measured for color properties is mounted on a die or button mount 22 upon a removable platform 24 which is positioned within the fixture 20 of fixture assembly 10. The term button is defined to include buttons, snaps, studs and the like.

The fixture 20 has a micrometer 26 which is easily rotated by turning knurled knob 28 for determining the position of the platform 24 relative to the color measuring instrument. The fixture also has a second knurled knob 86 which moves platform cylinder 38 in a vertical direction to orient the platform 24 in a preferred vertical position.

Figure 2:
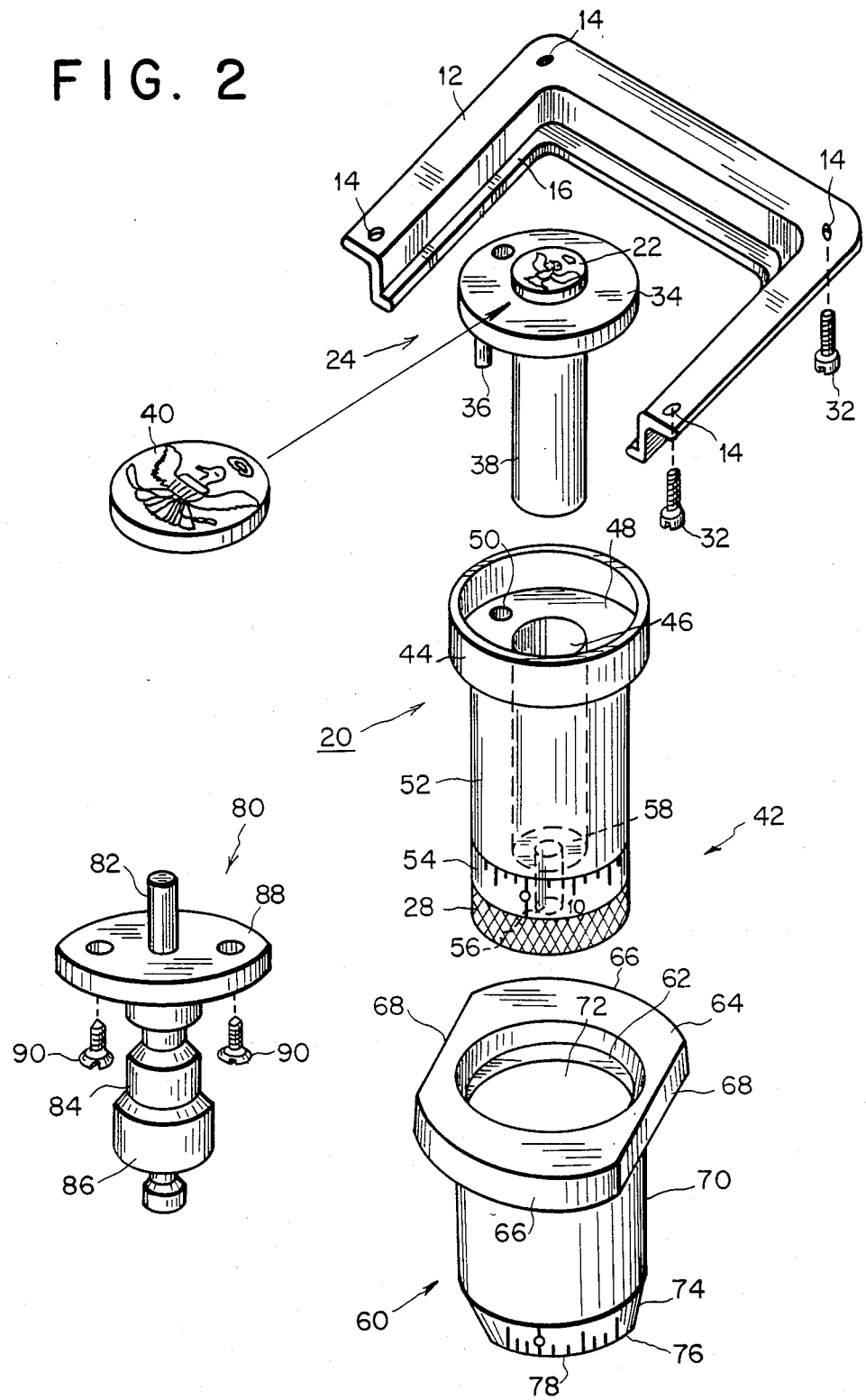
FIG. 2 is an exploded perspective view of the apparatus of FIG. 1, illustrating its various subassemblies.

FIG. 2 illustrates the component parts of the fixture assembly 10. Bracket 12 is fastened to the color measuring instrument at the four holes 14 by screws 32 or other fastening means. The inner shelf 16 of the bracket is also clearly shown.

Platform assembly 24 includes a platform 34, having guide pins 36, cylinder 38, and button mount 22. The button mount 22 is attached to platform 34 and holds button 40 in a fixed position on platform 34, while the guide pins 36 orient the platform 34 within the platform assembly 24. This mount 22 and guide pin 36 arrangement enables the button 40 to be repeatedly positioned in the same orientation with respect to the instrument.

The fixture 20 also includes a body 42 for holding platform assembly 24. The body 42 includes a top cup portion 44 and a hollow central core 46. The base 48 of cup portion 44 is provided with a hole 50 for receiving guide pin 36. Cylinder 38 of platform assembly 24 slides downwardly into the hollow central core 46 of body 42 with the guide pin 36 of the platform 34 engaging the hole 50 in the base 48 of the cup portion 44. Mount 22 then becomes seated on the base 48 of cup portion 44.

Body 42 also includes an elongated cylinder 52 which is graduated into 360 degrees 54 to form half of the micrometer 26. The end of cylinder 52 is knurled 28 to facilitate rotation in either horizontal direction.

Hollow central core 46 is not uniform throughout the cylinder and includes a reduced diameter hole 56 at the lower portion of cylinder 52. The junction between smaller hole 56 and hollow central core 46 provides a seat 58 below which platform cylinder 38 cannot pass. This seat 58 provides the lowest position for platform 34 as will be explained in detail hereinbelow.

The fixture 20 also includes a housing 60 for holding the platform assembly 24 and body 42. After the platform assembly 24 is placed in body 42, the body 42 is inserted into housing 60. The cup portion 44 of body 42 then rests on shelf 62 of the upper portion 64 of housing 60.

The upper portion 64 of housing 60 has generally arcuate portions 66 and flat portions 68. The flat portions 68 of the upper portion 64 of housing 60 enables the entire fixture assembly 20 to be slidably inserted into and out of bracket 12 for positioning within the color measuring instrument for measuring the color properties of the button 22.

Housing 60 also has an elongated cylindrical portion 70 and a centrally located hollow or open portion 72. This hollow portion 72 receives body 42.

The bottom 74 of the elongated cylindrical portion 70 of housing 60 is tapered so that the inner diameter of the end 76 of the housing 60 is slightly larger than the outer diameter of the bottom of the body 42. Also, this end 76 is provided with graduations 78 to form the other half of micrometer 26.

The final part of the fixture 20 is the vertical adjustment micrometer assembly 80. This assembly 80 includes a shaft 82 for moving platform cylinder 38 upwardly or downwardly in a vertical direction. The shaft 82 extends through the body 84 of the assembly 80 and is secured to knurled end 86. As the knurled end 86 is rotated, the shaft 80 moves incrementally in the desired upward or downward direction.

Also attached to body 84 is a flange 88 for attaching the assembly 80 by screws or bolts 90 to the base of the body 42 of the fixture 20. Alternately, other means of attaching the micrometer assembly to the body such as a set screw onto a cylindrical shaft could also be used. As can be appreciated from the arrangement, the vertical micrometer 80 rotates with cylinder 52 of body 42.

Figure 3:
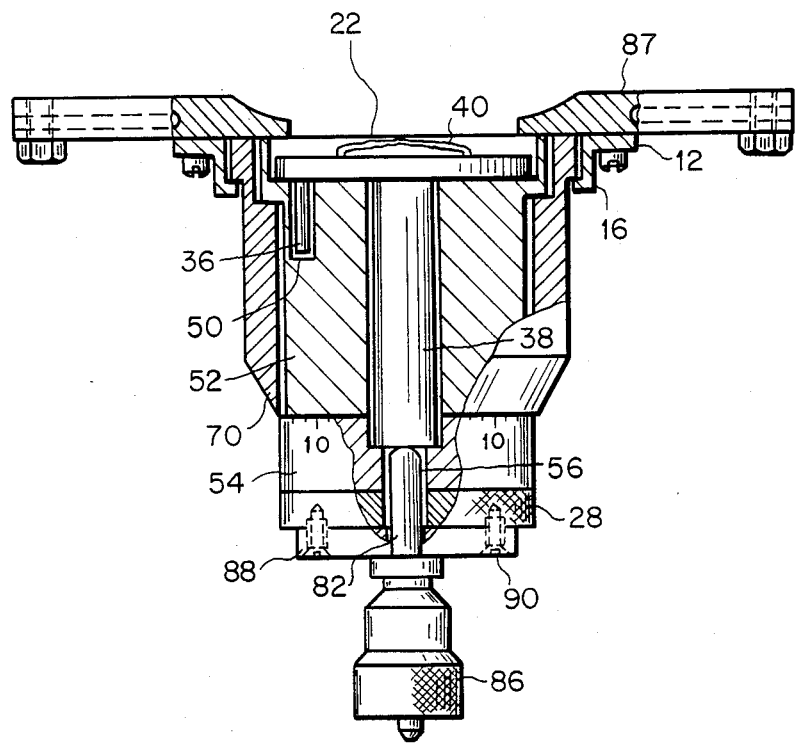
FIG. 3 is a cross sectional view of the apparatus taken along lines 3—3 of FIG. 1.

FIG. 3 shows the fixture assembly 10 fixedly attached to a plate 87 provided by the manufacturer located on the color measuring instrument to thus anchor the fixture assembly 10 to the instrument.

A preferred embodiment of the present invention entails placing an ornamental or decorative metal object such as a button over the corresponding male die 22 which is secured onto platform 34 of platform assembly 24. The entire fixture 20 is then slid into bracket 12 which is attached to a color measuring instrument.

The position of the metal object is then recorded in the following manner:

Knurled knob 28 of micrometer 26 is turned until a consistent color reading for the ornamental or decorative metal object is obtained on the measuring instrument. The position of the object on the horizontal axis is then recorded for purposes of orientation. Next, the knurled end 86 of the vertical adjustment micrometer assembly 80 is turned until the highest L value is obtained for the object by the instrument. This orientation is then also recorded by reading the micrometer. These positions are then used to check production materials against standard materials, such as metal plated buttons, which are kept on file.

An example of the method by which the fixture assembly apparatus is used to fixably position metal plated standard buttons for a comparison of their color properties with representative production buttons is described hereinbelow:

EXAMPLE

A button is placed onto the raised button mount of matching configuration which is affixed to the top of the removable platform of the fixture assembly of the invention. The fixture assembly is then slid into the bracket attached to a colorimeter such as a Hunter Lab D-25 colorimeter. The orientation of the button is then recorded in the following manner:

The knurled knob of the horizontal adjustment micrometer is turned until a consistent color reading for a or b is obtained. The resultant angle, which corresponds to the x and y position of the button is then recorded.

| Position | x,y | 34° |
|---|---|---|
| Color | a | b |
| | 0.8 | 0.6 |

Next, the vertical micrometer is turned until the highest point of the convex button is tangent to the plane of the view point. The lowest allowable distance from the plane of the view port should not exceed 1/64". The L value obtained on the colorimeter printer and the micrometer reading of the platform position is then recorded.

| Position | x,y | 34° |
|---|---|---|
| | z | 0.125 |
| Color | L | a | b |
| | 42.5 | 0.8 | 0.6 |

These readings then become the standard reference values for the particular button. Thereafter, a statistical sampling of production buttons can be measured for color properties and the measured values compared to the reference values. When testing the production samples, the same position is set on the colorimeter to check the color properties of production buttons against the standard values.

While it is apparent that the invention herein disclosed is well calculated to achieve the desired results, it will be appreciated that numerous modifications and embodiments may be devised by those skilled in the art, and it is intended that the appended claims cover all such modifications and embodiments as fall within the true spirit and scope of the present invention.

I claim:

1. An apparatus for reproducibly positioning an object within a color measurement instrument comprising:
   means for attaching the apparatus to a color measurement system;
   means for orienting an object in a predetermined fixed position on support means;
   means for determining the horizontal position of the object;
   means for determining the vertical position of the object,
   the horizontal and vertical position of the object being variable by moving the support means in horizontal and/or vertical directions so that optimum color properties of the object can be determined.

2. The apparatus according to claim 1 wherein the horizontal and vertical position determination means each comprise micrometer means.

3. The apparatus according to claim 1 wherein the object is a button.

4. The apparatus according to claim 1 wherein the means for attachment to the color measuring instrument is bracket means.

5. The apparatus according to claim 1 wherein the color measuring instrument is a colorimeter.

6. An apparatus for supporting an object for reproducible color measurement which comprises:
   bracket means attached to a color measuring instrument;
   platform means;
   means for orienting an object in a predetermined fixed position on the platform means;

means for synchronizing rotation of the platform means with the rotation of the object horizontal position determination means;

means to determine the horizontal position of the object; and means for determining the vertical position of the object said means being operable independent of the means for determining the horizontal position of the object and further being operable without changing the horizontal position of the object, the horizontal and vertical position determination means being variable by moving the platform means in horizontal and/or vertical directions so that optimum color properties of the object can be determined.

7. The apparatus according to claim 6 wherein the means for synchronizing rotation of the platform means with the rotation of the horizontal position determination means comprises at least two guide pins.

8. The apparatus according to claim 6 wherein said horizontal and vertical position determination means each comprise micrometer means.

9. A method for measuring the color properties of an object which comprises:
placing and orienting an object in a predetermined fixed position on the support means of an apparatus comprising:
means for attaching the apparatus to a color measurement system;
means for orienting an object in a predetermined fixed position on support means;
means for determining the horizontal position of the object;
means for determining the vertical position of the object;
the horizontal and vertical position of the object being variable by moving the support means in horizontal and/or vertical directions so that optimum color properties of the object can be determined;
attaching the apparatus to a color measurement system;
varying the horizontal and vertical positions of the object by moving the support means in horizontal and/or vertical directions to obtain the optimum color properties of the object; and
recording the horizontal and vertical position of the object at the optimum color properties.

10. The method according to claim 9 wherein the object is a button.

11. The method according to claim 9 wherein the attachment means is bracket means.

12. The method according to claim 9 wherein the means for varying the horizontal position of the object is micrometer means and the means for varying the vertical position of the object is also micrometer means.

13. The method according to claim 9 wherein the suport means is a die configured for reception of the object.

14. The method according to claim 9 wherein the color measurement system is a colorimeter.

15. A method for measuring color of an object which comprises:
placing the object on orientation means of an apparatus comprising:
bracket means attached to a color measuring instrument;
platform means;
means for orienting an object in a predetermined fixed position on the platform means;
means for synchronizing rotation of the platform means with the rotation of the object horizontal position determination means;
means for determine the horizontal position of the object; and
means for determining the vertical position of object, said means being operable independent of the means for determining the horizontal position of the object and further being operable without changing the horizontal position of the object;
the horizontal and vertical position determination means being variable by moving the platform means in horizontal and/or vertical directions so that optimum color properties of the object can be determined;
synchronizing the rotation of the platform means with the rotation of the horizontal position determination means;
determining the horizontal position of the object;
determining the vertical position of the object by means operable independent of the means for determining the horizontal position of the object and further being operable without changing the horizontal position of the object;
varying the horizontal and vertical position of the orientation means by moving the platform means in horizontal and/or vertical directions so that optimum color properties of the object can be determined; and
recording the horizontal and vertical position of the object at the optimum color properties.

16. The method according to claim 15 wherein the object is a button.

17. The method according to claim 15 wherein the orientation means is a die configured for reception of the object.

18. The method according to claim 15 wherein the rotation of the platform means is synchronized with the rotation of the horizontal position determination means by at least two guide pins.

19. The method according to claim 15 wherein the horizontal position of the object is adjusted by micrometer means.

20. The method according to claim 15 wherein the vertical position of an object is adjusted by micrometer means.

21. In a method for measuring the color properties of an object, the improvement which comprises reproducibly determining the optimum color properties of the object by providing an apparatus comprising:
means for attaching the apparatus to a color measurement system;
means for orienting an object in a predetermined fixed position on support means;
means for determining the horizontal position of the object;
means for determining the vertical position of the object;
the horizontal and vertical position of the object being variable by moving the support means in horizontal and/or vertical directions so that optimum color properties of the object can be determined;
wherein the object can be mounted on the mounting means in only one configuration and the horizontal and vertical position determination means can be preset to the predetermined position which displays the optimum color properties.

22. In a method for measuring the color properties of an object, the improvement which comprises reproducibly determining the optimum color properties of the object by providing an apparatus comprising:
bracket means attached to a color measuring instrument;
platform means;
means for orienting an object in a predetermined fixed position on the platform means;
means for synchronizing rotation of the platform means with the rotation of the object horizontal position determination means;
means to determine the horizontal position of the object; and
means for determining the vertical position of the object said means operable independent of the means for determining the horizontal position of the object and further being operable without changing the horizontal position of the object;
the horizontal and vertical position determination means being variable by moving the platform means in horizontal and/or vertical directions so that optimum color properties of the object can be determined;
wherein the object can be mounted on the mounting means in only one configuration and the horizontal and vertical position determination means can be preset to the predetermined position which displays the optimum color properties.

23. A quality control system which comprises:
predetermining the optimum color properties of a first object by:
placing and orienting an object in a predetermined fixed position on the support means of an apparatus comprising:
means for attaching the apparatus to a color measurement system;
means for orienting an object in a predetermined fixed position on support means;
means for determining the horizontal position of the object;
means for determining the vertical position of the object;
the horizontal and vertical position of the object being variable by moving the support means in horizontal and/or vertical directions so that optimum color properties of the object can be determined;
attaching the apparatus to a color measurement system;
varying the horizontal and vertical positions of the object by moving the support means in horizontal and/or vertical directions to obtain the optimum color properties of the object;
recording the horizontal and vertical position of the object at the optimum color properties;
selecting a representative sample of objects from a production run;
measuring the color properties of each member of the representative sample at the orientation previously recorded for the first object; and
comparing the properties of the sample with those of the first object.

24. The quality control system according to claim 23 wherein the color properties of the sample objects are statistically averaged before comparison with the properties of the first object.

25. A quality control system which comprises:
predetermining the optimum color properties of a first object by:
placing the object on the orientation means of an apparatus comprising:
bracket means attached to a color measuring instrument;
platform means;
means for orienting an object in a predetermined fixed position on the platform means;
means for synchronizing rotation of the platform means with the rotation of the object horizontal position determination means;
means for determine the horizontal position of the object; and
means for determining the vertical position of object, said means being operable independent of the means for determining the horizontal position of the object and further being operable without changing the horizontal position of the object;
the horizontal and vertical position determination means being variable by moving the platform means in horizontal and/or vertical directions so that optimum color properties of the object can be determined;
synchronizing the rotation of the platform means with the rotation of the horizontal position determination means;
determining the horizontal position of the object;
determining the vertical position of the object by means operable independent of the means for determining the horizontal position of the object and further being operable without changing the horizontal position of the object;
varying the horizontal and vertical position of the orientation means by moving the platform means in horizontal and/or vertical directions so that optimum color properties of the object can be determined;
recording the horizontal and vertical position of the object at the optimum color properties;
selecting a representative sample of objects from a production run;
measuring the color properties of each member of the representative sample at the orientations previously recorded for the first object; and
comparing the properties of the sample with those of the first object.

* * * * *